(12) United States Patent
Paul et al.

(10) Patent No.: US 9,126,196 B2
(45) Date of Patent: Sep. 8, 2015

(54) COMPOSITION INCLUDING DIALKYL TIN OXIDE AND USE THEREOF AS A TRANSESTERIFICATION CATALYST FOR THE SYNTHESIS OF (METH) ACRYLIC ESTERS

(75) Inventors: Jean-Michel Paul, Metz (FR); Boris Tonnelier, Guerting (FR); Francis Augustin, Lindre-Basse (FR)

(73) Assignee: Arkema France, Colombes (FR)

( * ) Notice: Subject to any disclaimer, the term of this patent is extended or adjusted under 35 U.S.C. 154(b) by 892 days.

(21) Appl. No.: 13/321,829

(22) PCT Filed: May 18, 2010

(86) PCT No.: PCT/FR2010/050949
§ 371 (c)(1),
(2), (4) Date: Feb. 1, 2012

(87) PCT Pub. No.: WO2010/136696
PCT Pub. Date: Dec. 2, 2010

(65) Prior Publication Data
US 2012/0123148 A1    May 17, 2012

(30) Foreign Application Priority Data
May 26, 2009    (FR) ...................................... 09 53433

(51) Int. Cl.
*C07C 67/03* (2006.01)
*B01J 31/12* (2006.01)

(52) U.S. Cl.
CPC ................ *B01J 31/122* (2013.01); *B01J 31/12* (2013.01); *C07C 67/03* (2013.01); *B01J 2231/49* (2013.01); *B01J 2531/42* (2013.01)

(58) Field of Classification Search
CPC .... C07C 67/03; B01J 2231/49; B01J 2531/42
See application file for complete search history.

(56) References Cited

U.S. PATENT DOCUMENTS

| | | |
|---|---|---|
| 3,642,877 A | 2/1972 | Jayawant |
| 7,078,560 B2 | 7/2006 | Houben et al. |
| 2006/0173191 A1 | 8/2006 | Curtis |

FOREIGN PATENT DOCUMENTS

| | | | |
|---|---|---|---|
| JP | 56104851 A | 8/1981 | |
| JP | 3118352 A | 5/1991 | |
| JP | 2001187763 A | 12/1999 | |

*Primary Examiner* — Robert Havlin
(74) *Attorney, Agent, or Firm* — Lynn B. Morreale

(57) ABSTRACT

The present invention relates to a composition including a dialkyl tin oxide, such as DBTO, which can be used as a transesterification catalyst for the synthesis of (meth)acrylic esters. The invention also relates to a method for the synthesis of (meth)acrylic esters by transesterification in the presence of said composition.

9 Claims, No Drawings

COMPOSITION INCLUDING DIALKYL TIN OXIDE AND USE THEREOF AS A TRANSESTERIFICATION CATALYST FOR THE SYNTHESIS OF (METH) ACRYLIC ESTERS

CROSS-REFERENCE TO RELATED APPLICATIONS

This application is a national stage application under 35 U.S.C. §371 of PCT/FR2010/050949, filed May 18, 2010, which claims benefit to French application FR 0953433, filed on May 26, 2009, all of which are hereby incorporated by reference.

FIELD OF THE INVENTION

The present invention relates to a composition comprising a dialkyltin oxide which can be used as transesterification catalyst for the synthesis of (meth)acrylic esters. The invention also relates to a process for the synthesis of (meth)acrylic esters by transesterification in the presence of this composition.

BACKGROUND OF THE INVENTION

Organic tin derivatives, in particular dialkyltin oxides, such as dibutyltin oxide ($Bu_2Sn=O$, referred to hereinafter as DBTO), are widely described in the literature as transesterification catalysts for the synthesis of (meth)acrylic esters.

DBTO is provided in the form of a white powder which is insoluble in water and virtually insoluble in alcohols, such as methanol or ethanol, or aminoalcohols, in hydrocarbon solvents and in (meth)acrylic esters, such as methyl acrylate or dimethylaminoethyl acrylate. It dissolves slowly in alkaline solutions; it is dissolved in carboxylic acids, with which it forms carboxylated derivatives.

DBTO in the solid form is widely used in transesterification processes of batch type. The use thereof is relatively simple in this case, although, however, it has to be handled with care due to its pulverulent state, which can result in risks of inhalation of a product exhibiting a toxicity related to that of tin.

The use of DBTO in the solid form proves to be more difficult in the case of a continuous transesterification process or when it is necessary to introduce DBTO continuously. Solutions exist, for example for the use of a system for introducing the powder via an endless screw, but these solutions are very awkward and do not obviate risks of inhalation of fine particles of tin-based compound.

The Applicant Company has found a simple and original means for using DBTO in the form of a concentrated solution. For this reason, it becomes easy to continuously introduce it in the form of a solution using a simple pump with all the advantages which this represents in terms of ease of processing and of health.

The use of organic tin derivatives, in particular DBTO and its homologs, in the synthesis of (meth)acrylic esters is widely described in the literature.

Mention may be made of the patent application JP 56-104851, which describes the use of a tin oxide, in particular DBTO, as transesterification catalyst in the synthesis of tert-butylaminoethyl methacrylate from methyl methacrylate and tert-butylaminoethanol.

The U.S. Pat. No. 3,642,877 describes the use of DBTO as catalyst in the synthesis of dimethylaminoethyl methacrylate by transesterification between methyl methacrylate and N,N-dimethylaminoethanol. DBTO is used in the solid form and it is introduced into the reaction medium only after an azeotropic distillation of the water with the methyl methacrylate has been carried out in order to prevent any deactivation of the DBTO by the water present in the reactants.

The patent application JP-A1-3-118,352 describes a process for the synthesis of dialkylaminoalkyl esters of (meth)acrylic acid by transesterification in a solvent which is inert to the reaction, such as hexane, under a pressure of 1.5 to 3 atmospheres, in the presence of powdered DBTO as catalyst.

Provision has been made, in the patent application US 2006/0173191, to introduce the transesterification catalyst, such as DBTO, in the form of several charges into the reaction reactor, the catalyst being introduced in the solid form, or as a mixture with crude reaction product withdrawn from the reactor, or else in the form of a suspension in methyl methacrylate. Under these conditions, the use of DBTO in concentrated homogeneous solution is not suggested.

In the patent application JP 2001-187763, the (meth)acrylic acid corresponding to the targeted (meth)acrylic ester is used to dissolve a dialkyltin oxide before being introduced in the solution form as transesterification catalyst, which makes it possible to avoid any problem of reprecipitation or of deposition of solid when the reaction temperature decreases.

The U.S. Pat. No. 7,078,560 claims the use of organic tin derivatives in the form of distannoxanes as transesterification catalysts in the synthesis of aminoalkyl (meth)acrylates for overcoming the problem of insolubility of DBTO in N,N-dimethylaminoethanol and more generally in aminoalcohols. The distannoxane is obtained by reaction of an organic tin oxide with its corresponding tin halide. By way of example, octabutyltetrachlorodistannoxane is prepared from DBTO and dibutyltin dichloride ($Bu_2SnCl_2$). This distannoxane can be dissolved at a level of 10% by weight or more in N,N-dimethylaminoethanol. According to this method, DBTO, in order to be dissolved in N,N-dimethylaminoethanol, has to be converted beforehand into another chemical entity, namely a distannoxane, which results in a complex preparation for the catalyst.

The Applicant Company has found a simpler means targeted at dissolving dibutyltin oxide at relatively concentrated contents, so as to generate catalytic solutions capable of being used directly in transesterification reactions.

Surprisingly, while DBTO is insoluble in alcohols and esters, it has been found that dibutyltin oxide dissolves in an alcohol/(meth)acrylic ester(s) mixture. This is the case, for example, for a mixture of alcohol and of methyl or ethyl (meth)acrylate, taken alone or in the presence of the heavy ester resulting from the transesterification reaction between the methyl or ethyl (meth)acrylate and the alcohol.

It is thus an aim of the present invention to provide a concentrated solution of dialkyltin oxide, more particularly of DBTO, which is homogeneous and stable over time at ambient temperature and which meets the health and safety requirements of legislation for the industrial sphere.

The aim of the present invention is also to provide a catalytic composition comprising DBTO or a homolog which can be used for the synthesis of (meth)acrylic esters by transesterification, which composition is prepared beforehand with pure compounds which can be employed in this synthesis, exhibiting an ease of use in a process of continuous type or when introduction of the catalyst continuously is necessary, and resulting in an improved selectivity with respect to solid DBTO or its homolog.

DETAILED DESCRIPTION OF CERTAIN EMBODIMENTS OF THE INVENTION

A subject matter of the present invention is a composition in the form of a solution which is stable over time at ambient temperature, comprising by weight, the total coming to 100%:
- from 5% to 75% of a dialkyltin oxide, the linear or branched alkyl chain having from 1 to 8 carbon atoms,
- from 10% to 80% of an alcohol $R_1OH$ (I), it being possible for $R_1$ to be a linear or branched alkyl radical, or a cyclic aliphatic, aryl, alkylaryl or arylalkyl radical, comprising from 4 to 40 carbon atoms, or a linear or branched alkyl radical comprising at least one heteroatom and from 3 to 40 carbon atoms,
- from 10% to 80% of a light alkyl (meth)acrylate (II), the linear or branched alkyl chain having from 1 to 4 carbon atoms,
- from 0 to 80% of a (meth)acrylic ester (III) comprising a radical which can be a linear or branched alkyl radical, or a cyclic aliphatic, aryl, alkylaryl or arylalkyl radical, comprising from 4 to 40 carbon atoms, or a linear or branched alkyl radical comprising at least one heteroatom and from 3 to 40 carbon atoms.

The term "(meth)acrylate" is understood to mean acrylic acid or methacrylic acid derivatives.

Use may be made, as dialkyltin oxide, of dimethyltin oxide, methylethyltin oxide, diethyltin oxide, dipropyltin oxide, di(n-butyl)tin oxide or dioctyltin oxide. Use is preferably made of a dialkyltin oxide with a linear alkyl chain having from 1 to 4 carbon atoms, more particularly of di(n-butyl)tin oxide (DBTO).

Advantageously, the composition comprises from 50% to 70% by weight of dialkyltin oxide, preferably from 55% to 65%. Within these concentration ranges, the solutions obtained are stable at ambient temperature, that is to say that they do not give rise to precipitation of solid.

Mention may be made, as alcohols (I) which can be used, without this list being limiting, of butanol, 2-ethylhexanol, decanol or aminoalcohols, such as N,N-dimethylaminoethanol, N,N-dimethylaminopropanol, N,N-diethylaminoethanol or tert-butylaminoethanol. Preferably, use is made of an aminoalcohol, such as N,N-dimethylaminoethanol.

Use may be made, as light alkyl (meth)acrylate (II), of methyl (meth)acrylate, ethyl (meth)acrylate or isopropyl (meth)acrylate, preferably methyl (meth)acrylate or ethyl (meth)acrylate.

Optionally, the composition comprises a (meth)acrylic ester (III) which can preferably be chosen from alkyl (meth)acrylates having a linear or branched chain comprising from 4 to 8 carbon atoms, such as butyl (meth)acrylate, 2-ethylhexyl (meth)acrylate or aminoalkyl (meth)acrylates, such as dimethylaminoethyl acrylate (DAMEA), dimethylaminopropyl acrylate, diethylaminoethyl acrylate, tert-butylaminoethyl acrylate or dimethylaminoethyl methacrylate (DAMEMA). Use is preferably made of dimethylaminoethyl acrylate (DAMEA).

The respective contents of alcohol, of light alkyl (meth)acrylate and of (meth)acrylic ester depend on the nature of the products used to carry out the dissolution of the dialkyltin oxide. Preferably, the composition according to the invention comprises by weight, the total coming to 100%:
- from 50% to 70% of a dialkyltin oxide, preferably of DBTO,
- from 10% to 40% of an alcohol $R_1OH$ (I),
- from 10% to 40% of a light alkyl (meth)acrylate (II),
- from 0 to 40% of a (meth)acrylic ester (III).

A preferred composition comprises by weight, the total coming to 100%:
- from 55% to 65% of DBTO,
- from 10% to 20% of an alcohol $R_1OH$ (I),
- from 10% to 20% of a light alkyl (meth)acrylate (II),
- from 0 to 20% of a (meth)acrylic ester (III).

The alcohol (I) is preferably N,N-dimethylaminoethanol and the (meth)acrylic ester (III) is preferably DAMEA or DAMEMA.

The composition according to the invention is obtained by heating, with stirring, at a temperature of between 80° C. and 130° C. and until dissolution is achieved, a mixture composed of dialkyltin oxide, in particular DBTO, of an alcohol $R_1OH$ (I), of a light alkyl (meth)acrylate (II) and also preferentially, in order to accelerate the dissolution, of a (meth)acrylic ester (III).

More specifically, the composition according to the invention is prepared by introducing DBTO, or its homolog, on one or more than one occasion and with vigorous stirring, at ambient temperature or in hot conditions, at atmospheric pressure or under slight negative pressure, into the alcohol $R_1OH$/light alkyl (meth)acrylate mixture, with or without (meth)acrylic ester, and by then heating the mixture at a temperature of between 80° C. and 130° C. until a clear solution is obtained. When dissolution has been carried out, heating can be prolonged for a few hours before cooling to ambient temperature.

The homogeneous solution obtained is stored at ambient temperature, preferably with the exclusion of light, without giving rise to precipitation of solid.

It is preferable to protect the (meth)acrylic derivatives present in the composition according to the invention from polymerization using polymerization inhibitors, the action of which can be promoted by bubbling air into the mixture, in particular depleted air comprising 8% by volume of $O_2$.

Use may be made, without implied limitation, as polymerization inhibitors, of hydroquinone, hydroquinone methyl ether, 2,6-di(tert-butyl)-4-methylphenol (BHT), phenothiazine, 2,2,6,6-tetramethyl-1-piperidinyloxyl (TEMPO) or its derivatives, or para-phenylenediamine, alone or as a mixture, in a proportion of 100 to 5000 ppm, preferably of 500 to 3000 ppm, for each inhibitor introduced into the mixture.

The composition according to the invention is advantageously used as catalytic composition for the synthesis of (meth)acrylic esters by transesterification of a light alkyl (meth)acrylate with an alcohol.

The choice of the products used to carry out the dissolution of the DBTO will preferably be adjusted to the nature of the (meth)acrylic ester which will be synthesized using this solution as catalyst. In all cases, "pure" products are involved and not phases withdrawn from a crude reaction mixture.

Thus, it is preferable to use the alcohol which will be employed for the transesterification. For example, when a DBTO solution for catalyzing the synthesis of DAMEA from methyl acrylate (MA) or ethyl acrylate (EA) and N,N-dimethylaminoethanol is prepared, use will be made of N,N-dimethylaminoethanol by way of alcohol $R_1OH$ (I).

Likewise, use will preferably be made, for (II) and (III), respectively of the light alkyl (meth)acrylate which will be employed for the synthesis of the (meth)acrylic ester by transesterification and of the ester thus produced.

In the preceding case, use will be made, for (II), of methyl acrylate or ethyl acrylate and, for (III), of N,N-dimethylaminoethyl acrylate (DAMEA).

Thus it is that solutions comprising 60-70% by weight of DBTO could be prepared by heating DBTO in a mixture of N,N-dimethylaminoethyl, methyl acrylate and N,N-dimethylaminoethyl acrylate, said solutions subsequently being used directly to manufacture DAMEA in a continuous process.

In the case where the DBTO solution will be used to catalyze the synthesis of butyl acrylates by transesterification between EA and butanol, the choice will respectively be made, for (I), of butanol, for (II), of ethyl acrylate and, for (III), of butyl acrylate.

Another subject matter of the present invention is a process for the synthesis of (meth)acrylic esters of formula (III):

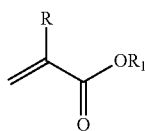

in which R is a hydrogen atom or a methyl group and $R_1$ is a linear or branched alkyl radical, or a cyclic aliphatic, aryl, alkylaryl or arylalkyl radical, comprising from 4 to 40 carbon atoms, or a linear or branched alkyl radical comprising at least one heteroatom and from 3 to 40 carbon atoms,
by a transesterification reaction of a light alkyl (meth)acrylate of formula (II):

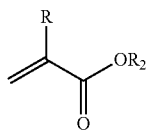

in which R has the abovementioned meanings and $R_2$ is a linear or branched alkyl chain having from 1 to 4 carbon atoms,
with an alcohol of formula (I):

in which $R_1$ has the abovementioned meanings,
in the presence of a transesterification catalyst, characterized in that the catalyst is a composition in the form of a solution which is stable over time at ambient temperature, as described above.

Preferably, the catalytic composition is based on DBTO.

The amount of catalytic composition to be used is calculated from the number of moles of DBTO to be employed per mole of alcohol $R_1OH$ employed in the transesterification reaction.

The molar amount of DBTO is between 0.001 and 0.02 mol/mol of alcohol $R_1OH$ employed in the transesterification reaction, preferably between 0.005 and 0.015 mol/mol of alcohol $R_1OH$.

The process according to the invention is used in particular to prepare dimethylaminoethyl acrylate (DAMEA), dimethylaminopropyl acrylate, diethylaminoethyl acrylate, tert-butylaminoethyl acrylate or dimethylaminoethyl methacrylate (DAMEMA), preferably DAMEA.

Preferably, the light alkyl (meth)acrylate (II) is methyl acrylate or ethyl acrylate.

Methanol or ethanol is generated during the synthesis, which material is removed in the form of an azeotrope with methyl acrylate or ethyl acrylate (II) respectively.

In the process according to the invention, the choice is preferably made of a molar ratio of methyl or ethyl (meth) acrylate (II) to alcohol (I) of between 2 and 5, preferably between 2 and 4.

The reaction temperature is generally between 80° C. and 130° C. and the pressure is generally maintained between 2 kPa and atmospheric pressure. Preferably, the reaction temperature is between 90° C. and 110° C. and the pressure is of the order of from 50 kPa to atmospheric pressure.

The reaction is generally carried out in the presence of at least one polymerization inhibitor. Use is made, as polymerization inhibitor, of phenothiazine, hydroquinone, hydroquinone monomethyl ether, di(tert-butyl)-para-cresol (BHT), para-phenylenediamine, TEMPO (2,2,6,6-tetramethyl-1-piperidinyloxyl), di(tert-butyl)catechol or TEMPO derivatives, alone or as a mixture, in a proportion of from 100 to 5000 ppm, with respect to the initial charge, preferably between 500 and 3000 ppm.

When the operation is carried out continuously, the reactants (I) and (II) optionally comprising polymerization inhibitors are introduced continuously, as a mixture or separately, using pump(s). The catalytic composition is introduced separately using a pump, at ambient temperature or under hot conditions at a temperature of between ambient temperature and 80° C.

The reaction can be carried out in a mechanically stirred reactor or by forced circulation. The reaction mixture is heated using a jacket or by forced circulation through an external exchanger. The reactor is surmounted by a distillation column equipped with a top condenser, with a reflux head and with a vacuum receiver having a collecting vessel and trap.

The process according to the invention is particularly advantageous since there is no formation of solid precipitate capable of blocking the pipes during the reaction and results in improved selectivities with respect to those obtained with solid DBTO.

The following examples illustrate the present invention without, however, limiting the scope thereof. The percentages are expressed as percentages by weight.

EXAMPLES

The following abbreviations are used:
MA: methyl acrylate
EA: ethyl acrylate
BuA: butyl acrylate
MMA: methyl methacrylate
AOH: N,N-dimethylaminoethanol
DAMEA: N,N-dimethylaminoethyl acrylate
DAMEMA: N,N-dimethylaminoethyl methacrylate
PTZ: phenothiazine
HQME: hydroquinone methyl ether
BHT: 2,6-di(tert-butyl)-4-methylphenol Example 1

The following are charged to a mechanically stirred glass reactor equipped with a jacket:
125 g of N,N-dimethylaminoethanol (AOH)
145 g of methyl acrylate (MA)
125 g of N,N-dimethylaminoethyl acrylate (DAMEA)
600 g of DBTO
3 g of PTZ
2 g of HQME The mixture is subsequently heated with stirring by circulation of oil thermostatically controlled at 110° C. in the jacket.

After 1 h 30 min, the medium is completely clear and homogeneous. The solution is left stirring for a further 30 min and is then cooled. The solution is stored at ambient temperature with the exclusion of light before use as catalyst. There is no precipitation of solid. This solution could be used for several weeks without observing a phenomenon of deactivation.

Example 2

A solution is prepared under the same conditions as those of example 1, which solution comprises:
125 g of N,N-dimethylaminoethanol (AOH)
145 g of methyl methacrylate (MMA)
125 g of N,N-dimethylaminoethyl methacrylate (DAMEMA)
600 g of DBTO
3 g of PTZ
2 g of HQME

Example 3

A solution is prepared under the same conditions as those of example 1, which solution comprises:
125 g of n-butanol
145 g of ethyl acrylate (EA)
125 g of butyl acrylate (BuA)
600 g of DBTO
3 g of PTZ
2 g of HQME

Example 4

Example 1 is repeated with:
125 g of N,N-dimethylaminoethanol (AOH)
125 g of methyl acrylate (MA)
280 g of DBTO
1.6 g of PTZ
1.1 g of HQME The mixture is heated at 100° C. for 4 h until a clear solution is obtained. The solution is left stirring for an additional 30 min and is then cooled. The solution is stored at ambient temperature with the exclusion of light.

Example 5

Synthesis of DAMEA from MA

The catalytic solution of example 1 is used to prepare DAMEA by transesterification between MA and AOH.

The reaction is carried out in a stirred glass reactor heated by circulation of thermostatically controlled oil in a jacket and surmounted by a distillation column equipped with a condenser, reflux head, vacuum receiver, collecting vessel and trap.

The reactor is charged with MA (432.7 g), AOH (279.9 g), the polymerization inhibitors (PTZ 4000 ppm, BHT 2000 ppm) and the catalytic solution prepared in example 1 (13.05 g, i.e. 0.01 mol of DBTO/mole of AOH employed for the reaction).
MA/AOH molar ratio: 1.6/1

The methanol formed is distilled off in the form of an MA/methanol azeotrope as it is formed, in order to shift the reaction equilibrium.

The reaction is carried out by adjusting the pressure in order not to exceed 110° C. in the reactor.

The crude product is subsequently distilled under a pressure from 13 kPa to 8 kPa.

Four successive operations are carried out by charging MA and AOH to the distillation residue comprising the inhibitors and the catalyst.

|  | OP No. 1 | OP No. 2 | OP No. 3 | OP No. 4 |
| --- | --- | --- | --- | --- |
| AOH conversion, % | 84.5 | 90 | 88.2 | 86.6 |
| Reaction time, h | 3 | 3.5 | 4 | 4 |

Example 6

Synthesis of BuA from EA

The apparatus described in example 5 is used.

The reactor is charged with EA (494.2 g), butanol (228.6 g), the inhibitors (PTZ 4000 ppm, BHT 2000 ppm) and the catalytic solution of example 3 (12.8 g, i.e. 0.01 mol of DBTO/mole of butanol employed for the reaction).
EA/butanol molar ratio: 1.6/1

The ethanol formed is distilled off in the form of an EA/ethanol azeotrope as it is formed in order to shift the reaction equilibrium.

The reaction is carried out by adjusting the pressure in order not to exceed 110° C. in the reactor.

The crude product is subsequently distilled under a pressure from 13 kPa to 8 kPa.
Reaction time: 4 h 30 min
Conversion of butanol: 99.3%
Selectivity for BuA: 99.5%

Example 7

Synthesis of DAMEMA from MMA

The apparatus described in example 5 is used.

The reactor is charged with MMA (581.2 g), AOH (258.6 g), the inhibitors (PTZ 4000 ppm, BHT 2000 ppm) and the catalytic solution of example 2 (12.1 g, i.e. 0.01 mol of DBTO/mole of AOH).
MMA/AOH molar ratio: 1.6/1

The methanol formed is distilled off in the form of an MMA/methanol azeotrope as it is formed in order to shift the reaction equilibrium.

The reaction is carried out by adjusting the pressure in order not to exceed 110° C. in the reactor.

The crude product is subsequently distilled under a pressure from 13 kPa to 8 kPa.
Reaction time: 5 h 30 min
Conversion of AOH: 99.7%
Selectivity for DAMEMA: 95.5%

Example 8

Continuous Synthesis of DAMEA from MA

The apparatus is similar to that used for tests 5 to 7. The mixture of reactants (MA, AOH, inhibitors) is introduced continuously into the reactor using a pump at a flow rate of 156.7 g/h.

The catalytic solution of example 1 is introduced via a pump at a flow rate of 3.1 g/h.

The methanol formed is distilled off in the form of an MA/methanol azeotrope as it is formed, in order to shift the reaction equilibrium.
MA/AOH molar ratio: 1.4/1

Catalyst: 0.01 mol of DBTO/mole of AOH
Passage time in the reactor: 6 h
Inhibitors: PTZ 3000 ppm/BHT 1000 ppm
T°: 95° C.
Duration of the test: 72 h The crude reaction product is subsequently distilled. The residue comprising the catalyst is recycled continuously in the following test.

The light distillation fractions are recycled in the following test with a contribution of fresh MA and AOH. 90% of the residue comprising the catalyst is recycled with a supplementary amount of fresh catalytic solution.

Three tests were carried out under these conditions:

|  | Test 1 | Test 2 | Test 3 |
|---|---|---|---|
| Duration of the test, h | 72 | 47 | 24 |
| Conversion of AOH, % | 68.6 | 70.2 | 72.5 |
| Composition of the crude product at the outlet of the reactor, % | | | |
| MeOH | 0.3 | 0.3 | 0.2 |
| MA | 13.7 | 12.0 | 11.2 |
| AOH | 18.2 | 15.1 | 14.3 |
| DAMEA | 60.8 | 60.5 | 60.2 |

Example 9

Comparative

The synthesis of example 5 is reproduced using solid DBTO. The DBTO/AOH molar ratio is equal to 0.01 in both examples.

|  | Example 9 Solid DBTO 7.7 g per 279.9 g of AOH | Example 5 (OP No. 1) DBTO as a 60% solution 12.8 g of solution i.e., 7.7 g of DBTO per 279.9 g of AOH |
|---|---|---|
| Reaction time, h | 4 | 3 |
| AOH conversion, % | 83.2 | 84.5 |
| DAMEA selectivity, % | 92.7 | 94.9 |

The invention claimed is:

1. A composition in the form of a homogeneous solution which is storable for at least 24 hours at ambient temperature with the exclusion of light and without precipitation of solids, said composition comprising by weight, the total coming to 100%:
   from 50% to 70% of dibutyltin oxide,
   from 10% to 40% of an alcohol $R_1OH$ (I), wherein $R_1$ is a linear or branched alkyl radical, or a cyclic aliphatic, aryl, alkylaryl or arylalkyl radical, having from 4 to 40 carbon atoms, or a linear or branched alkyl radical having at least one heteroatom and from 3 to 40 carbon atoms,
   from 10% to 40% of an alkyl (meth)acrylate (II), wherein the alkyl is a linear or branched alkyl chain having from 1 to 4 carbon atoms, and
   from 0 to 40% of a (meth)acrylic ester (III) which is one or more alkyl (meth)acrylates wherein the alkyl is a linear or branched alkyl radical, or a cyclic aliphatic, aryl, alkylaryl or arylalkyl radical, having from 4 to 40 carbon atoms, or a linear or branched alkyl radical having at least one heteroatom and from 3 to 40 carbon atoms.

2. The composition as claimed in claim 1, comprising:
   from 50% to 70% of a dialkyltin oxide,
   from 10% to 40% of an alcohol $R_1OH$ (I),
   from 10% to 40% of an alkyl (meth)acrylate (II) selected from the group consisting of methyl (meth)acrylate, ethyl (meth)acrylate, and isopropyl (meth)acrylate, and
   from 0 to 40% of a (meth)acrylic ester (III).

3. The composition as claimed in claim 1, wherein the alcohol (I) is selected from the group consisting of butanol, 2 ethylhexanol, decanol, N,N dimethylaminoethanol, N,N dimethylaminopropanol, N,N diethylaminoethanol, and tert-butylaminoethanol.

4. The composition as claimed in claim 1, wherein the alkyl (meth)acrylate (II) is methyl (meth)acrylate or ethyl (meth)acrylate.

5. The composition as claimed in claim 1, wherein the (meth)acrylic ester (III) is an alkyl (meth)acrylate wherein the alkyl is a linear or branched chain having from 4 to 8 carbon atoms and optionally at least one heteroatom.

6. The composition as claimed in claim 5 wherein the (meth)acrylic ester (III) is selected from the group consisting of butyl (meth)acrylate, 2 ethylhexyl (meth)acrylate, dimethylaminoethyl acrylate (DAMEA), dimethylaminopropyl acrylate, diethylaminoethyl acrylate, tert-butylaminoethyl acrylate and dimethylaminoethyl methacrylate (DAMEMA).

7. A method of synthesizing (meth)acrylic esters comprising using the composition of claim 1 in a transesterification reaction of the alkyl (meth)acrylate with the alcohol.

8. The method as claimed in claim 7 wherein the (meth) acrylic ester (III) is a product of the transesterification reaction.

9. The method as claimed in claim 7 wherein the composition for synthesis comprises by weight, the total coming to 100%:
   from 55% to 65% of DBTO,
   from 10% to 20% of N,N-dimethylaminoethanol,
   from 10% to 20% of methyl (meth)acrylate or ethyl (meth)acrylate,
   from 0 to 20% of dimethylaminoethyl (meth)acrylate,
whereby dimethylaminoethyl (meth)acrylate is produced from the transesterification of N,N dimethylaminoethanol and methyl (meth)acrylate or ethyl (meth)acrylate.

* * * * *